(12) United States Patent
Dijkstra

(10) Patent No.: US 11,185,033 B2  
(45) Date of Patent: Nov. 30, 2021

(54) HYBRID SPINACH 'E03D.1051'

(71) Applicant: Enza Zaden Beheer B.V., Enkhuizen (NL)

(72) Inventor: Jan Ane Dijkstra, Enkhuizen (NL)

(73) Assignee: Enza Zaden Beheer B.V., Enkhuizen (NL)

(*) Notice: Subject to any disclaimer, the term of this patent is extended or adjusted under 35 U.S.C. 154(b) by 1 day.

(21) Appl. No.: 16/726,100

(22) Filed: Dec. 23, 2019

(65) Prior Publication Data

US 2021/0185958 A1 Jun. 24, 2021

(51) Int. Cl.
*A01H 6/02* (2018.01)
*A01H 5/10* (2018.01)

(52) U.S. Cl.
CPC ............. *A01H 6/028* (2018.05); *A01H 5/10* (2013.01)

(58) Field of Classification Search
None
See application file for complete search history.

(56) References Cited

U.S. PATENT DOCUMENTS

| | | | |
|---|---|---|---|
| 5,777,196 A | 7/1998 | Hall | |
| 5,948,957 A | 9/1999 | Chapko et al. | |
| 5,959,185 A | 9/1999 | Streit et al. | |
| 5,969,212 A | 10/1999 | Getschman | |
| 5,973,234 A | 10/1999 | Mueller et al. | |
| 5,977,445 A | 11/1999 | Soper et al. | |
| 9,295,219 B2 * | 3/2016 | Braber | A23L 19/03 |

FOREIGN PATENT DOCUMENTS

| | | |
|---|---|---|
| WO | WO-2018059651 A1 | 4/2018 |
| WO | WO-2018060445 A1 | 4/2018 |
| WO | WO-2019063839 A1 | 4/2019 |
| WO | WO-2020239572 A1 | 12/2020 |

OTHER PUBLICATIONS

Enza Zaden USA, Inc. Jan. 2020. 'E03D.1042', 'E03D.1047', and 'E03D.1051'. Vegetable Seed Catalogue USA & Canada 2020. Available online at <https://webkiosk.enzazaden.com/catalogue-usa-2020/62983894>, Obtained on Jul. 24, 2020. p. 37.

Feng et al., (2018). "New Races and Novel Strains of the Spinach Downy Mildew Pathogen Peronospora effusa", Plant Disease, 102(3):613-618.

She et al., (2018). "Fine mapping and candidate gene screening of the downy mildew resistance gene RPF1 in Spinach", Theor Appl Genet., 131(12):2529-2541.

* cited by examiner

*Primary Examiner* — Russell T Boggs
(74) *Attorney, Agent, or Firm* — Morrison & Foerster LLP

(57) ABSTRACT

Hybrid spinach 'E03D.1051' is described. The invention relates to the seeds of hybrid spinach 'E03D.1051', to the plants of hybrid spinach 'E03D.1051', to methods for producing hybrid plants, and to methods for producing other spinach lines, cultivars or hybrids derived from the hybrid spinach 'E03D.1051'.

12 Claims, 6 Drawing Sheets
(6 of 6 Drawing Sheet(s) Filed in Color)

HYBRID SPINACH 'E03D.1051'

FIELD

This invention relates to the field of plant breeding. In particular, this invention relates to new and distinctive spinach (*Spinacia oleracea* L.) hybrids designated 'E03D.1042', 'E03D.1047', and 'E03D.1051'.

BACKGROUND

Spinach (*Spinacia oleracea* L.) is an annual flowering plant in the Amaranthaceae family. Spinach is cultivated worldwide, mostly in regions with temperate climates. The edible part of the spinach plant are the leaves which are produced during the first stage of the plant's life cycle, the vegetative rosette stage. Spinach leaves are eaten raw or cooked, and can be sold loose, bunched, washed and packaged in containers, frozen, or as canned products. Spinach is one of the most desirable dark green leafy vegetables due to its highly nutritious leaves, which are a good source of beta-carotene, folate, vitamin B2, vitamin B6, vitamin E, calcium, potassium and dietary fiber. The second stage of the plant's life cycle is the flowering stage, or the bolting stage. When bolting occurs the plant will allocate its resources to flowering instead of leaf production, which will ultimately cause the leaves to wither and make harvesting of marketable leaves no longer possible. Fast bolting is thus a very undesired trait in the production of spinach Based on the leaf texture and shape, there are three basic types of spinach, namely savoy, semi-savoy, and smooth. The savoy type has dark green, crinkly, and curly leaves, the semi-savoy type has slightly crinkled leaves, while the smooth type (also known as flat type), has broad and smooth leaves. Spinach is unusual among vegetables in that it is a dioecious species, with individual plants producing either all male or all female flowers. Occasionally, spinach also produces monoecious plants with both male and female flowers. The gender in the species is regulated by the XY chromosome system. Commercial cultivars were initially open-pollinated as spinach is a naturally wind-pollinated plant, but most have now been replaced by better yielding hybrids.

Like many other vegetables, spinach production is affected by a number of diseases. Downy mildew, caused by *Peronospora farinosa* f sp. *spinaciae*, is a particularly widespread and destructive disease in spinach, causing significant economic losses annually to the spinach industry. Downy mildew is especially damaging for spinach production since it causes necrotic lesions on the edible leaves, can spread very rapidly, and cause breakdown and rot of the infected leaves when packaged in containers. In recent years, various resistance genes have been identified that provide spinach plants with a resistance against downy mildew. However, it has been shown that *Peronospora farinosa* f. sp. *spinaciae* is rapidly evolving to overcome resistance in commercial spinach cultivars. Since 2014, three more new pathogenic races of *Peronospora farinosa* f. sp. *spinaciae* have been reported, making a total of 17 races of *Peronospora farinosa* f. sp. *spinaciae* (designated races pfs1 to pfs17). Therefore, new sources or novel patterns of downy mildew resistance are highly sought after to overcome rapidly evolving downy mildew in spinach.

Spinach is an economically important and valuable vegetable crop. Thus, there is a continued need for new spinach varieties. In particular, there is a need for improved spinach varieties that are stable, high yielding, downy mildew resistant, and agronomically sound.

SUMMARY OF THE INVENTION

In order to meet these needs, the present invention is directed to improved spinach varieties.

In one embodiment, the present invention is directed to spinach, *Spinacia oleracea* L., seed designated as 'E03D.1042' having NCIMB Accession Number X1. In one embodiment, the present invention is directed to a spinach plant and parts isolated therefrom produced by growing 'E03D.1042' spinach seed. In another embodiment, the present invention is directed to a spinach plant and parts isolated therefrom having all the physiological and morphological characteristics of a spinach plant produced by growing 'E03D.1042' spinach seed having NCIMB Accession Number X1. In still another embodiment, the present invention is directed to an $F_1$ hybrid *Spinacia oleracea* L. spinach seed, plants grown from the seed, and leaves isolated therefrom having 'E03D.1042' as a parent, wherein 'E03D.1042' is grown from 'E03D.1042' spinach seed having NCIMB Accession Number X1.

Spinach plant parts include leaves, parts of spinach leaves, ovules, pollen, cotyledons, embryos, meristems, anthers, roots, root tips, pistils, flowers, stems, calli, hypocotyls, and the like. In another embodiment, the present invention is further directed to spinach leaves, parts of spinach leaves, stems, roots, root tips, pollen, ovules, and flowers isolated from 'E03D.1042' spinach plants. In a further embodiment, the present invention is directed to a plant or plant parts of 'E03D.1042' harvested at baby leaf stage. In another embodiment, the present invention is further directed to spinach plants regenerated from tissue culture, where the plant has all of the morphological and physiological characteristics of 'E03D.1042' spinach plants. In yet another embodiment, the present invention is further directed to spinach plants grown from vegetative propagation by taking part of 'E03D.1042' plant and allowing that plant part to form roots, where the plant has all of the morphological and physiological characteristics of 'E03D.1042' spinach plants.

In still another embodiment, the present invention is further directed to packaging material containing 'E03D.1042' plant parts. Such packaging material includes but is not limited to boxes, plastic bags, etc. The 'E03D.1042' plant parts may be combined with other plant parts of other plant varieties.

In yet another embodiment, the present invention is further directed to a method of selecting spinach plants by a) growing 'E03D.1042' spinach plants wherein the 'E03D.1042' plants are grown from spinach seed having NCIMB Accession Number X1; and b) selecting a plant from step a). In another embodiment, the present invention is further directed to spinach plants, plant parts and seeds produced by the spinach plants, where the spinach plants are isolated by the selection method of the invention.

In another embodiment, the present invention is further directed to a method of breeding spinach plants by crossing a spinach plant with a plant grown from 'E03D.1042' spinach seed having NCIMB Accession Number X1. In still another embodiment, the present invention is further directed to spinach plants, spinach parts from the spinach plants, and seeds produced therefrom where the spinach plant is isolated by the breeding method of the invention.

In another embodiment, the present invention is directed to methods of introducing a desired trait into spinach hybrid 'E03D.1042', by: (a) crossing a 'E03D.1042' plant, where a sample of 'E03D.1042' spinach seed was deposited under NCIMB Accession Number X1, with a plant of another spinach variety that contains a desired trait to produce progeny plants, where the desired trait is selected from salinity resistance; reduced Cd uptake; reduced oxalate content; male sterility; herbicide resistance; insect or pest resistance; modified bolting; and resistance to bacterial disease, fungal disease or viral disease; (b) selecting one or more progeny plants that have the desired trait; (c) backcrossing the selected progeny plants with a 'E03D.1042' plant to produce backcross progeny plants; (d) selecting for backcross progeny plants that have the desired trait and all of the physiological and morphological characteristics of spinach hybrid 'E03D.1042'; and (e) repeating steps (c) and (d) two or more times in succession to produce selected third or higher backcross progeny plants that comprise the desired trait. Certain embodiments are also directed to spinach plants produced by such methods, where the plants have the desired trait and all of the physiological and morphological characteristics of spinach hybrid 'E03D.1042'.

In another embodiment, the present invention is directed to methods for producing a seed of a hybrid spinach variety 'E03D.1042'-derived spinach plant comprising the steps of: (a) crossing a spinach plant of hybrid variety 'E03D.1042', representative seed of which having been deposited under NCIMB Accession Number X1, with a second spinach plant or with itself; and (b) allowing seed of a hybrid variety 'E03D.1042'-derived spinach plant to form. In still another embodiment, the methods for producing a seed of a hybrid spinach variety 'E03D.1042'-derived spinach plant further comprising the steps of: (c) selfing the plant grown from said hybrid variety 'E03D.1042'-derived spinach seed or crossing it to a second spinach plant to yield additional hybrid variety 'E03D.1042'-derived spinach seed; (d) growing said additional hybrid variety 'E03D.1042'-derived spinach seed of step (c) to yield additional 'E03D.1042'-derived spinach plants; and (e) repeating the crossing and growing steps of (c) and (d) for an additional 3-10 generations to generate further 'E03D.1042'-derived spinach plants, and (f) allowing further seed of a hybrid variety 'E03D.1042'-derived spinach plant to form.

In one embodiment, the present invention is directed to spinach, *Spinacia oleracea* L., seed designated as 'E03D.1047' having NCIMB Accession Number X2. In one embodiment, the present invention is directed to a spinach plant and parts isolated therefrom produced by growing 'E03D.1047' spinach seed. In another embodiment, the present invention is directed to a spinach plant and parts isolated therefrom having all the physiological and morphological characteristics of a spinach plant produced by growing 'E03D.1047' spinach seed having NCIMB Accession Number X2. In still another embodiment, the present invention is directed to an $F_1$ hybrid *Spinacia oleracea* L. spinach seed, plants grown from the seed, and leaves isolated therefrom having 'E03D.1047' as a parent, wherein 'E03D.1047' is grown from 'E03D.1047' spinach seed having NCIMB Accession Number X2.

Spinach plant parts include leaves, parts of spinach leaves, ovules, pollen, cotyledons, embryos, meristems, anthers, roots, root tips, pistils, flowers, stems, calli, hypocotyls, and the like. In another embodiment, the present invention is further directed to spinach leaves, parts of spinach leaves, stems, roots, root tips, pollen, ovules, and flowers isolated from 'E03D.1047' spinach plants. In a further embodiment, the present invention is directed to a plant or plant parts of 'E03D.1047' harvested at baby leaf stage. In another embodiment, the present invention is further directed to spinach plants regenerated from tissue culture, where the plant has all of the morphological and physiological characteristics of 'E03D.1047' spinach plants. In yet another embodiment, the present invention is further directed to spinach plants grown from vegetative propagation by taking part of 'E03D.1047' plant and allowing that plant part to form roots, where the plant has all of the morphological and physiological characteristics of 'E03D.1047' spinach plants.

In still another embodiment, the present invention is further directed to packaging material containing 'E03D.1047' plant parts. Such packaging material includes but is not limited to boxes, plastic bags, etc. The 'E03D.1047' plant parts may be combined with other plant parts of other plant varieties.

In yet another embodiment, the present invention is further directed to a method of selecting spinach plants by a) growing 'E03D.1047' spinach plants wherein the 'E03D.1047' plants are grown from spinach seed having NCIMB Accession Number X2; and b) selecting a plant from step a). In another embodiment, the present invention is further directed to spinach plants, plant parts and seeds produced by the spinach plants, where the spinach plants are isolated by the selection method of the invention.

In another embodiment, the present invention is further directed to a method of breeding spinach plants by crossing a spinach plant with a plant grown from 'E03D.1047' spinach seed having NCIMB Accession Number X2. In still another embodiment, the present invention is further directed to spinach plants, spinach parts from the spinach plants, and seeds produced therefrom where the spinach plant is isolated by the breeding method of the invention.

In another embodiment, the present invention is directed to methods of introducing a desired trait into spinach hybrid 'E03D.1047', by: (a) crossing a 'E03D.1047' plant, where a sample of 'E03D.1047' spinach seed was deposited under NCIMB Accession Number X2, with a plant of another spinach variety that contains a desired trait to produce progeny plants, where the desired trait is selected from salinity resistance; reduced Cd uptake; reduced oxalate content; male sterility; herbicide resistance; insect or pest resistance; modified bolting; and resistance to bacterial disease, fungal disease or viral disease; (b) selecting one or more progeny plants that have the desired trait; (c) backcrossing the selected progeny plants with a 'E03D.1047' plant to produce backcross progeny plants; (d) selecting for backcross progeny plants that have the desired trait and all of the physiological and morphological characteristics of spinach variety 'E03D.1047'; and (e) repeating steps (c) and (d) two or more times in succession to produce selected third or higher backcross progeny plants that comprise the desired trait. Certain embodiments are also directed to spinach plants produced by such methods, where the plants have the desired trait and all of the physiological and morphological characteristics of spinach hybrid 'E03D.1047'.

In another embodiment, the present invention is directed to methods for producing a seed of a hybrid spinach variety 'E03D.1047'-derived spinach plant comprising the steps of: (a) crossing a spinach plant of hybrid variety 'E03D.1047', representative seed of which having been deposited under NCIMB Accession Number X2, with a second spinach plant or with itself; and (b) allowing seed of a hybrid variety 'E03D.1047'-derived spinach plant to form. In still another embodiment, the methods for producing a seed of a hybrid spinach variety 'E03D.1047'-derived spinach plant further comprising the steps of: (c) selfing the plant grown from said hybrid variety 'E03D.1047'-derived spinach seed or crossing it to a second spinach plant to yield additional hybrid variety 'E03D.1047'-derived spinach seed; (d) growing said additional hybrid variety 'E03D.1047'-derived spinach seed of step (c) to yield additional 'E03D.1047'-derived spinach plants; and (e) repeating the crossing and growing steps of (c) and (d) for an additional 3-10 generations to generate further 'E03D.1047'-derived spinach plants, and (f) allowing further seed of a hybrid variety 'E03D.1047'-derived spinach plant to form.

In one embodiment, the present invention is directed to spinach, *Spinacia oleracea* L., seed designated as 'E03D.1051' having NCIMB Accession Number 43578. In one embodiment, the present invention is directed to a spinach plant and parts isolated therefrom produced by growing 'E03D.1051' spinach seed. In another embodiment, the present invention is directed to a spinach plant and parts isolated therefrom having all the physiological and morphological characteristics of a spinach plant produced by growing 'E03D.1051' spinach seed having NCIMB Accession Number 43578. In still another embodiment, the present invention is directed to an $F_1$ hybrid *Spinacia oleracea* L. spinach seed, plants grown from the seed, and leaves isolated therefrom having 'E03D.1051' as a parent, wherein 'E03D.1051' is grown from 'E03D.1051' spinach seed having NCIMB Accession Number 43578.

Spinach plant parts include leaves, parts of spinach leaves, ovules, pollen, cotyledons, embryos, meristems, anthers, roots, root tips, pistils, flowers, stems, calli, hypocotyls, and the like. In another embodiment, the present invention is further directed to spinach leaves, parts of spinach leaves, stems, roots, root tips, pollen, ovules, and flowers isolated from 'E03D.1051' spinach plants. In a further embodiment, the present invention is directed to a plant or plant parts of 'E03D.1051' harvested at baby leaf stage. In another embodiment, the present invention is further directed to spinach plants regenerated from tissue culture, where the plant has all of the morphological and physiological characteristics of 'E03D.1051' spinach plants. In yet another embodiment, the present invention is further directed to spinach plants grown from vegetative propagation by taking part of 'E03D.1051' plant and allowing that plant part to form roots, where the plant has all of the morphological and physiological characteristics of 'E03D.1051' spinach plants.

In still another embodiment, the present invention is further directed to packaging material containing 'E03D.1051' plant parts. Such packaging material includes but is not limited to boxes, plastic bags, etc. The 'E03D.1051' plant parts may be combined with other plant parts of other plant varieties.

In yet another embodiment, the present invention is further directed to a method of selecting spinach plants by a) growing 'E03D.1051' spinach plants wherein the 'E03D.1051' plants are grown from spinach seed having NCIMB Accession Number 43578; and b) selecting a plant from step a). In another embodiment, the present invention is further directed to spinach plants, plant parts and seeds produced by the spinach plants, where the spinach plants are isolated by the selection method of the invention.

In another embodiment, the present invention is further directed to a method of breeding spinach plants by crossing a spinach plant with a plant grown from 'E03D.1051' spinach seed having NCIMB Accession Number 43578. In still another embodiment, the present invention is further directed to spinach plants, spinach parts from the spinach plants, and seeds produced therefrom where the spinach plant is isolated by the breeding method of the invention.

In another embodiment, the present invention is directed to methods of introducing a desired trait into spinach hybrid 'E03D.1051', by: (a) crossing a 'E03D.1051' plant, where a sample of 'E03D.1051' spinach seed was deposited under NCIMB Accession Number 43578, with a plant of another spinach variety that contains a desired trait to produce progeny plants, where the desired trait is selected from salinity resistance; reduced Cd uptake; reduced oxalate content; male sterility; herbicide resistance; insect or pest resistance; modified bolting; and resistance to bacterial disease, fungal disease or viral disease; (b) selecting one or more progeny plants that have the desired trait; (c) backcrossing the selected progeny plants with a 'E03D.1051' plant to produce backcross progeny plants; (d) selecting for backcross progeny plants that have the desired trait and all of the physiological and morphological characteristics of spinach hybrid 'E03D.1051'; and (e) repeating steps (c) and (d) two or more times in succession to produce selected third or higher backcross progeny plants that comprise the desired trait. Certain embodiments are also directed to spinach plants produced by such methods, where the plants have the desired trait and all of the physiological and morphological characteristics of spinach hybrid 'E03D.1051'.

In another embodiment, the present invention is directed to methods for producing a seed of a hybrid spinach variety 'E03D.1051'-derived spinach plant comprising the steps of: (a) crossing a spinach plant of hybrid variety 'E03D.1051', representative seed of which having been deposited under NCIMB Accession Number 43578, with a second spinach plant or with itself; and (b) allowing seed of a hybrid variety 'E03D.1051'-derived spinach plant to form. In still another embodiment, the methods for producing a seed of a hybrid spinach variety 'E03D.1051'-derived spinach plant further comprising the steps of: (c) selfing the plant grown from said hybrid variety 'E03D.1051'-derived spinach seed or crossing it to a second spinach plant to yield additional hybrid variety 'E03D.1051'-derived spinach seed; (d) growing said additional hybrid variety 'E03D.1051'-derived spinach seed of step (c) to yield additional 'E03D.1051'-derived spinach plants; and (e) repeating the crossing and growing steps of (c) and (d) for an additional 3-10 generations to generate further 'E03D.1051'-derived spinach plants, and (f) allowing further seed of a hybrid variety 'E03D.1051'-derived spinach plant to form.

In a further embodiment, the present invention relates to methods for developing spinach plants in a spinach plant breeding program using plant breeding techniques including recurrent selection, backcrossing, pedigree breeding, restriction fragment length polymorphism enhanced selection, and genetic marker enhanced selection. Seeds, spinach plants, and parts thereof, produced by such breeding methods are also part of the invention.

In addition to the exemplary aspects and embodiments described above, further aspects and embodiments will become apparent by reference by study of the following description.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 1A shows plants of hybrid spinach 'E03D.1042' growing in the field. FIG. 1B shows leaves of hybrid spinach 'E03D.1042'.

FIG. 2A shows plants of hybrid spinach 'E03D.1047' growing in the field. FIG. 2B shows leaves of hybrid spinach 'E03D.1047'.

FIG. 3A shows plants of hybrid spinach 'E03D.1051' growing in the field. FIG. 3B illustrates leaves of hybrid spinach 'E03D.1051'.

DETAILED DESCRIPTION OF THE INVENTION

Figure 1A:
FIGS. 1A-1B show hybrid spinach 'E03D.1042'.

There are numerous steps in the development of novel, desirable spinach germplasm. Plant breeding begins with the analysis of problems and weaknesses of current spinach germplasms, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include greater yield, higher nutritional value, better growth rate and leaf properties, resistance to insect or pest, resistance to bacterial disease, fungal disease or viral disease, tolerance to drought and heat, and better agronomic quality.

Choice of breeding or selection methods can depend on the mode of plant reproduction, the heritability of the trait(s) being improved, and the type of variety used commercially (e.g., $F_1$ hybrid variety, pureline variety, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable variety. This approach has been used extensively for breeding disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program may include a periodic, objective evaluation of the efficiency of the breeding procedure. Evaluation criteria vary depending on the goal and objectives, and can include gain from selection per year based on comparisons to an appropriate standard, the overall value of the advanced breeding lines, and the number of successful varieties produced per unit of input (e.g., per year, per dollar expended, etc.).

Promising advanced breeding lines may be thoroughly tested and compared to appropriate standards in environments representative of the commercial target area(s) for at least three years. The best lines can then be candidates for new commercial varieties. Those still deficient in a few traits may be used as parents to produce new populations for further selection. These processes, which lead to the final step of marketing and distribution, may take from ten to twenty years from the time the first cross or selection is made.

One goal of spinach plant breeding is to develop new, unique, and genetically superior spinach varieties. A breeder can initially select and crosses two or more parental lines, followed by repeated selfing and selection, producing many new genetic combinations. Moreover, a breeder can generate multiple different genetic combinations by crossing, selfing, and mutations. A plant breeder can then select which germplasms to advance to the next generation. These germplasms may then be grown under different geographical, climatic, and soil conditions, and further selections can be made during, and at the end of, the growing season.

The development of commercial spinach varieties thus requires the development of parental spinach varieties, the crossing of these varieties, and the evaluation of the crosses. Pedigree breeding and recurrent selection breeding methods may be used to develop varieties from breeding populations. Breeding programs can be used to combine desirable traits from two or more varieties or various broad-based sources into breeding pools from which new varieties are developed by selfing and selection of desired phenotypes. The new varieties are crossed with other varieties and the hybrids from these crosses are evaluated to determine which have commercial potential.

Pedigree breeding is generally used for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population. Then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new varieties.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding may be used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines with each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques known in the art that are available for the analysis, comparison and characterization of plant genotype. Such techniques include, without limitation, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs), which are also referred to as Microsatellites), and Single Nucleotide Polymorphisms (SNPs).

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding may also be used to introduce new traits into spinach varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company (1993).

The production of double haploids can also be used for the development of homozygous varieties in a breeding program. Double haploids are produced by the doubling of a set of chromosomes from a heterozygous plant to produce a completely homozygous individual. For example, see Wan, et al., *Theor. Appl. Genet.*, 77:889-892 (1989).

Additional non-limiting examples of breeding methods that may be used include, without limitation, those found in *Principles of Plant Breeding*, John Wiley and Son, pp. 115-161 (1960); Allard (1960); Simmonds (1979); Sneep, et al. (1979); Fehr (1987); and "Carrots and Related Vegetable Umbelliferae," Rubatzky, V. E., et al. (1999).

Definitions

In the description and tables that follow, a number of terms are used. In order to provide a clear and consistent understanding of the specification and claims, including the scope to be given such terms, the following definitions are provided.

Allele. The allele is any of one or more alternative form of a gene, all of which alleles relates to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Bolting. The premature development of a flowering stalk, and subsequent seed, before a plant produces a food crop. Bolting is typically caused by late planting.

Cotyledon. One of the first leaves of the embryo of a seed plant; typically one or more in monocotyledons, two in dicotyledons, and two or more in gymnosperms.

Essentially all the physiological and morphological characteristics. A plant having essentially all the physiological and morphological characteristics of another plant means a plant having the physiological and morphological characteristics, except for the characteristics derived from the converted gene, of the other plant.

Gene. As used herein, "gene" refers to a segment of nucleic acid. A gene can be introduced into a genome of a species, whether from a different species or from the same species, using transformation or various breeding methods.

*Peronospora farinosa* f. sp. *Spinaciae* (Pfs). An oomycete that causes downy mildew in spinach.

Quantitative Trait Loci (QTL). Quantitative trait loci refer to genetic loci that control to some degree numerically representable traits that are usually continuously distributed.

Regeneration. Regeneration refers to the development of a plant from tissue culture.

RHS. RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

Single gene converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Overview of Hybrid Spinach 'E03D.1042'

Figure 1B:

Hybrid spinach 'E03D.1042' is a light green colored spinach variety that has no red coloration of stem, petioles, or veins and absent or very weak blistering of leaf blade. 'E03D.1042' is suitable for open field cultivation and has an early time of start of bolting for spring sown crops. Additionally, hybrid spinach 'E03D.1042' is resistant to *Peronospora farinosa* f sp. *spinaciae* (Pfs, downy mildew) races Pfs:1-Pfs:17. FIGS. 1A-1B depict plants and leaves of hybrid spinach 'E03D.1042'. Hybrid spinach 'E03D.1042' is particularly characterized by its resistance to *Peronospora farinosa* f. sp. *spinaciae* and by its color.

Hybrid spinach 'E03D.1042' has shown uniformity and stability for the traits, within the limits of environmental influence for the traits. The hybrid has been increased with continued observation for uniformity. No variant traits have been observed or are expected in hybrid spinach 'E03D.1042'.

Objective Description of Hybrid Spinach 'E03D.1042'

Hybrid spinach 'E03D.1042' has the following morphologic and other characteristics:
Seed:
  Spines: Absent
  Surface texture: Smooth
Plant:
  Ploidy: Diploid
  Growth rate: Fast
  Market mature stage: Baby leaf
  Growth habit: Semi-erect
  Size: Medium
  Spread: 10 cm
  Height: 10 cm
  Red coloration of stem, petioles, and veins: Absent
Seedling cotyledon:
  Width: 5 mm
  Length: 40 mm
  Tip shape: Rounded
  Color: Medium green
First foliage leaves:
  Shape: Ovate
  Base shape: Lobed
  Tip shape: Round-pointed
  Margin: Flat
  Upper surface color: Medium green
  Lower surface color: Medium green
Market mature leaves (baby leaves):
  Surface texture: Smooth
  Shape: Ovate
  Base shape: V-shape
  Tip shape: Pointed
  Margin: Flat
  Upper surface color: Light green
  Lower surface color: Medium green
  Luster: Dull
  Leaf blade:
    Size: Medium
    Length: 5 cm
    Width: 4 cm
    Blade Lobing: Not lobed
    Cross-section: Flat
    Attitude: Semi-erect
  Petiole:
    Color: Medium green
    Anthocyanin pigmentation: Absent
    Attitude: Semi-erect
    Length to the blade: 10 cm
    Diameter: 5 mm
Seed stalk development:
  Time of start of bolting for spring sown crops (15% of plants): Early (comparable to Camaro (unpatented))
  Proportion of monoecious plants: 0-10%
  Proportion of female plants: 66-90%
  Proportion of male plants: 11-35%
  Number of leaves on stalk of female plant: Medium
  Number of leaves on stalk of male plant: Medium
Disease/Pest Resistance:
  Downy Mildew (*Peronospora farinosa* f sp. *spinaciae*) (Pfs): Resistant to Pfs:1-Pfs:17

Comparisons to Other Spinach Varieties

Table 1 below compares characteristics of hybrid spinach 'E03D.1042' with spinach variety 'Shelby' (unpatented). Column 1 lists the characteristics, column 2 shows the characteristics for hybrid spinach 'E03D.1042', and column 3 shows the characteristics for spinach variety 'Shelby'.

TABLE 1

| Characteristic | 'E03D.1042' | 'Shelby' |
| --- | --- | --- |
| Leaf blade intensity of green color | Light | Medium dark |
| *Peronospora farinosa* f sp. *spinaciae* (Pfs) resistance | Resistant to Pfs:1-Pfs:17 | Resistant to Pfs:1-Pfs:13; Pfs:15, and Pfs:16 |

Overview of Hybrid Spinach 'E03D.1047'

Figure 2A:
FIGS. 2A-2B show hybrid spinach 'E03D.1047'.
Figure 2B:

Hybrid spinach 'E03D.1047' is a medium green colored spinach variety that has no red coloration of stem, petioles, or veins and absent or very weak blistering of leaf blade. 'E03D.1047' is suitable for open field cultivation and has an early time of start of bolting for spring sown crops. Additionally, spinach hybrid 'E03D.1047' is resistant to *Peronospora farinosa* f sp. *spinaciae* (Pfs, downy mildew) races Pfs:1-Pfs:17. FIGS. 2A-2B depict plants and leaves of hybrid spinach 'E03D.1047'. Hybrid spinach 'E03D.1047' is particularly characterized by its resistance to *Peronospora farinosa* f. sp. *spinaciae*.

Hybrid spinach 'E03D.1047' has shown uniformity and stability for the traits, within the limits of environmental influence for the traits. The hybrid has been increased with continued observation for uniformity. No variant traits have been observed or are expected in hybrid spinach 'E03D.1047'.

Objective Description of Hybrid Spinach 'E03D.1047'

Hybrid spinach 'E03D.1047' has the following morphologic and other characteristics:
Seed:
  Spines: Absent
  Surface texture: Smooth
Plant:
  Ploidy: Diploid
  Growth rate: Fast
  Market mature stage: Baby leaf
  Growth habit: Semi-erect
  Size: Medium
  Spread: 10 cm
  Height: 15 cm
  Red coloration of stem, petioles, and veins: Absent
Seedling cotyledon:
  Width: 5 mm
  Length: 40 mm
  Tip shape: Rounded
  Color: Light green
First foliage leaves:
  Shape: Ovate
  Base shape: V-shape
  Tip shape: Round-pointed
  Margin: Flat
  Upper surface color: Medium green
  Lower surface color: Light green
Market mature leaves (baby leaves):
  Surface texture: Smooth
  Shape: Medium elliptic
  Base shape: Straight
  Tip shape: Pointed
  Margin: Flat
  Upper surface color: Medium green
  Lower surface color: Medium green
  Luster: Glossy Leaf blade:
  Size: Small
  Length: 5 cm
  Width: 3 cm
  Blade Lobing: Not lobed
  Cross-section: Flat
  Attitude: Erect
Petiole:
  Color: Light green
  Anthocyanin pigmentation: Absent
  Attitude: Semi-erect
  Length to the blade: 6 cm
  Diameter: 5 mm
Seed stalk development:
  Time of start of bolting for spring sown crops (15% of plants): Early (comparable to
  Camaro (unpatented))
  Proportion of monoecious plants: 0-10%
  Proportion of female plants: 91-100%
  Proportion of male plants: 0-10%
  Number of leaves on stalk of female plant: Medium
Disease/Pest Resistance:
  Downy Mildew (*Peronospora farinosa* f sp. *spinaciae*) (Pfs): Resistant to Pfs:1-Pfs:17

Comparisons to Other Spinach Varieties

Table 2 below compares characteristics of hybrid spinach 'E03D.1047' with spinach variety 'Shelby' (unpatented). Column 1 lists the characteristics, column 2 shows the characteristics for hybrid spinach 'E03D.1047', and column 3 shows the characteristics for spinach variety 'Shelby'.

TABLE 2

| Characteristic | 'E03D.1047' | 'Shelby' |
|---|---|---|
| Leaf blade intensity of green color | Medium | Medium dark |
| *Peronospora farinosa* f sp. *spinaciae* (Pfs) resistance | Resistant to Pfs:1-Pfs:17 | Resistant to Pfs:1-Pfs:13; Pfs:15, and Pfs:16 |

Overview of Hybrid Spinach 'E03D.1051'

Figure 3A:
FIGS. 3A-3B show hybrid spinach 'E03D.1051'.
Figure 3B:

Hybrid spinach 'E03D.1051' is a medium green colored spinach variety that has no red coloration of stem, petioles, or veins and medium blistering of leaf blade. 'E03D.1051' is suitable for open field cultivation and has an medium time of start of bolting for spring sown crops. Additionally, hybrid spinach 'E03D.1051' is resistant to *Peronospora farinosa* f. sp. *spinaciae* (Pfs, downy mildew) races Pfs:1-Pfs:17. FIGS. 3A-3B depict plants and leaves of hybrid spinach 'E03D.1051'. Hybrid spinach 'E03D.1051' is particularly characterized by its resistance to *Peronospora farinosa* f. sp. *spinaciae* and leaf texture.

Hybrid spinach 'E03D.1051' has shown uniformity and stability for the traits, within the limits of environmental influence for the traits. The hybrid has been increased with continued observation for uniformity. No variant traits have been observed or are expected in hybrid spinach 'E03D.1051'.

Objective Description of Hybrid Spinach 'E03D.1051'

Hybrid spinach 'E03D.1051' has the following morphologic and other characteristics:
Seed:
  Spines: Absent
  Surface texture: Smooth
Plant:
  Ploidy: Diploid
  Growth rate: Medium
  Market mature stage: Baby leaf
  Growth habit: Semi-erect
  Size: Medium
  Spread: 8 cm
  Height: 8 cm
  Red coloration of stem, petioles, and veins: Absent
Seedling cotyledon:
  Width: 5 mm
  Length: 50 mm
  Tip shape: Rounded
  Color: Light green
First foliage leaves:
  Shape: Ovate
  Base shape: Straight
  Tip shape: Round-pointed
  Margin: Slightly curled
  Upper surface color: Medium green
  Lower surface color: Light green
Market mature leaves (baby leaves):
  Surface texture: Semi-savoy
  Shape: Medium ovate
  Base shape: Straight
  Tip shape: Round-pointed
  Margin: Slightly curled
  Upper surface color: Medium green
  Lower surface color: Medium green
  Luster: Glossy
  Leaf blade:
    Size: Medium
    Length: 6 cm
    Width: 5 cm
    Cross-section: Flat
    Attitude: Semi-erect
  Petiole:
    Color: Light green
    Anthocyanin pigmentation: Absent
    Attitude: Semi-erect
    Length to the blade: 5 cm
    Diameter: 5 mm
  Seed stalk development:
    Time of start of bolting for spring sown crops (15% of plants): Medium (comparable to Acadia (unpatented))
    Proportion of monoecious plants: 100%
    Proportion of female plants: 0%
    Proportion of male plants: 0%
  Disease/Pest Resistance:
    Downy Mildew (*Peronospora farinosa* f sp. *spinaciae*) (Pfs): Resistant to Pfs:1-Pfs:17

Comparisons to Other Spinach Varieties

Table 3 below compares characteristics of hybrid spinach 'E03D.1051' with spinach variety 'Acadia' (unpatented). Column 1 lists the characteristics, column 2 shows the characteristics for hybrid spinach 'E03D.1051', and column 3 shows the characteristics for spinach variety 'Acadia'.

TABLE 3

| Characteristic | 'E03D.1051' | 'Acadia' |
|---|---|---|
| *Peronospora farinosa* f sp. *spinaciae* (Pfs) resistance | Resistant to Pfs:1-Pfs:17 | Resistant to Pfs:1-Pfs:13; Pfs:15, and Pfs:16 |

Further Embodiments

Harvested Plant Material

Harvested plant material refers herein to plant parts, especially leaves, which have been collected for further storage and/or further use. Marketable leaves may be harvested at any stage before the bolting or flowering stage. "Leaves" may refer to leaf blades, leaf petioles, leaf blades and leaf petioles, or any portion thereof.

Harvestable stage is clear to skilled spinach growers and refers to the leaf stage from baby leaf stage, through to mature leaf stage, before the spinach plant starts bolting and an inflorescence stem develops. At baby leaf stage the spinach plant typically has at least two fully grown leaves (i.e., true leaves that start developing after the cotyledons have been formed). The smaller and more tender leaves of this stage are appreciated by the customer. Baby leaf spinach is typically grown at a density of 8 million seeds/ha and harvested when the spinach plants are about 10 cm high, though baby leaf spinach may be harvested even earlier and/or grown at a different density.

Gene Conversions

When the term spinach plant, hybrid, cultivar or spinach line are used in the context of the present invention, this also includes any gene conversions of that variety. The term "gene converted plant" as used herein refers to those spinach plants which are developed by backcrossing, genetic engineering, or mutation, where essentially all of the desired morphological and physiological characteristics of a variety are recovered in addition to the one or more genes transferred into the variety via the backcrossing technique, genetic engineering, or mutation. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental spinach plant which contributes the gene for the desired characteristic is termed the "nonrecurrent" or "donor parent." This terminology refers to the fact that the nonrecurrent parent is used one time in the backcross protocol and therefore does not recur. The parental spinach plant to which the gene or genes from the nonrecurrent parent are transferred is known as the recurrent parent as it is used for several rounds in the backcrossing protocol (Poehlman & Sleper (1994) and Fehr (1993)). In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until a spinach plant is obtained where essentially all of the desired morphological and physiological characteristics of the recurrent parent are recovered in the converted plant, in addition to the transferred gene from the nonrecurrent parent.

The selection of a suitable recurrent parent is an important step for a successful backcrossing procedure. The goal of a backcross protocol is to alter or substitute a trait or characteristic in the original line. To accomplish this, a gene of the recurrent variety is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected in the development of a new line but that can be improved by backcrossing techniques. Examples of these traits include, but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability, and yield enhancement. These genes are generally inherited through the nucleus. Several of these gene traits are described in U.S. Pat. Nos. 5,777,196, 5,948,957, and 5,969,212, the disclosures of which are specifically hereby incorporated by reference.

Tissue Culture

Further reproduction of the variety can occur by tissue culture and regeneration. Tissue culture of various tissues of spinach and regeneration of plants therefrom is well known and widely published. For example, reference may be had to Teng, et al., *HortScience,* 27:9, 1030-1032 (1992); Teng, et al., *HortScience,* 28:6, 669-1671 (1993); Zhang, et al., *Journal of Genetics and Breeding,* 46:3, 287-290 (1992); Webb, et al., *Plant Cell Tissue and Organ Culture,* 38:1, 77-79 (1994); Curtis, et al., *Journal of Experimental Botany,* 45:279, 1441-1449 (1994); Nagata, et al., *Journal for the American Society for Horticultural Science,* 125:6, 669-672 (2000); and Ibrahim, et al., *Plant Cell Tissue and Organ Culture,* 28(2), 139-145 (1992). It is clear from the literature that the state of the art is such that these methods of obtaining plants are routinely used and have a very high rate of success. Thus, another aspect of this invention is to provide cells which upon growth and differentiation produce spinach plants having the physiological and morphological characteristics of hybrid 'E03D.1042', 'E03D.1047', or 'E03D.1051'.

As used herein, the term "tissue culture" indicates a composition containing isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture containing organs has been used to produce regenerated plants. U.S. Pat. Nos. 5,959,185, 5,973,234, and 5,977,445 describe certain techniques, the disclosures of which are incorporated herein by reference.

Additional Breeding Methods

The invention is also directed to methods for producing a spinach plant by crossing a first parent spinach plant with a second parent spinach plant where the first or second parent spinach plant is a spinach plant of hybrid 'E03D.1042', 'E03D.1047', or 'E03D.1051'. Further, both first and second parent spinach plants can come from spinach hybrid 'E03D.1042', 'E03D.1047', or 'E03D.1051'. Thus, any such methods using spinach hybrid 'E03D.1042', 'E03D.1047', or 'E03D.1051' are part of the invention: selfing, backcrosses, hybrid production, crosses to populations, and the like. All plants produced using spinach hybrid 'E03D.1042', 'E03D.1047', or 'E03D.1051' as at least one parent are within the scope of this invention, including those developed from varieties derived from spinach hybrid 'E03D.1042', 'E03D.1047', or 'E03D.1051'. Advantageously, this spinach cultivar could be used in crosses with other, different, spinach plants to produce the first generation ($F_1$) spinach hybrid seeds and plants with superior characteristics. The variety of the invention can also be used for transformation where exogenous genes are introduced and expressed by the variety of the invention. Genetic variants created either through traditional breeding methods using spinach hybrid 'E03D.1042', 'E03D.1047', or 'E03D.1051', or through transformation of hybrid 'E03D.1042', 'E03D.1047', or 'E03D.1051' by any of a number of protocols known to those of skill in the art are intended to be within the scope of this invention.

The following describes breeding methods that may be used with spinach hybrid 'E03D.1042', 'E03D.1047', or 'E03D.1051' in the development of further spinach plants. One such embodiment is a method for developing spinach hybrid 'E03D.1042', 'E03D.1047', or 'E03D.1051' progeny spinach plants in a spinach plant breeding program, by: obtaining the spinach plant, or a part thereof, of hybrid 'E03D.1042', 'E03D.1047', or 'E03D.1051', utilizing said plant or plant part as a source of breeding material, and selecting a spinach hybrid 'E03D.1042', 'E03D.1047', or 'E03D.1051' progeny plant with molecular markers in common with hybrid 'E03D.1042', 'E03D.1047', or 'E03D.1051' and/or with morphological and/or physiological characteristics selected from the characteristics listed in the section entitled "Objective Description of Hybrid Spinach 'E03D.1042'", "Objective Description of Hybrid Spinach 'E03D.1047'", or "Objective Description of Hybrid Spinach 'E03D.1051'". Breeding steps that may be used in the spinach plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of spinach hybrid 'E03D.1042', 'E03D.1047', or 'E03D.1051' progeny spinach plants, by crossing hybrid 'E03D.1042', 'E03D.1047', or 'E03D.1051' with another spinach plant, thereby producing a population of spinach plants, which, on average, derive 50% of their alleles from spinach hybrid 'E03D.1042', 'E03D.1047', or 'E03D.1051'. A plant of this population may be selected and repeatedly selfed or sibbed with a spinach variety resulting from these successive filial generations. One embodiment of this invention is the spinach variety produced by this method and that has obtained at least 50% of its alleles from spinach hybrid 'E03D.1042', 'E03D.1047', or 'E03D.1051'. One of ordinary skill in the art of plant breeding would know how to evaluate the traits of two plant varieties to determine if there is no significant difference between the two traits expressed by those varieties. For example, see Fehr and Walt, *Principles of Variety Development*, pp. 261-286 (1987). Thus the invention includes spinach hybrid 'E03D.1042', 'E03D.1047', or 'E03D.1051' progeny spinach plants containing a combination of at least two hybrid 'E03D.1042', 'E03D.1047', or 'E03D.1051' traits selected from those listed in the section entitled "Objective Description of Spinach Hybrid 'E03D.1042'", "Objective Description of Spinach Hybrid 'E03D.1047'", or "Objective Description of Spinach Hybrid 'E03D.1051'", or the hybrid 'E03D.1042', 'E03D.1047', or 'E03D.1051' combination of traits listed in the Summary of the Invention, so that said progeny spinach plant is not significantly different for said traits than spinach hybrid 'E03D.1042', 'E03D.1047', or 'E03D.1051' as determined at the 5% significance level when grown in the same environmental conditions. Using techniques described herein, molecular markers may be used to identify said progeny plant as a spinach hybrid 'E03D.1042', 'E03D.1047', or 'E03D.1051' progeny plant. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of spinach hybrid 'E03D.1042', 'E03D.1047', or 'E03D.1051' may also be characterized through their filial relationship with spinach hybrid 'E03D.1042', 'E03D.1047', or 'E03D.1051', as for example, being within a certain number of breeding crosses of spinach hybrid 'E03D.1042', 'E03D.1047', or 'E03D.1051'. A breeding cross is a cross made to introduce new genetics into the progeny, and is distinguished from a cross, such as a self or a sib cross, made to select among existing genetic alleles. The lower the number of breeding crosses in the pedigree, the closer the relationship between spinach hybrid 'E03D.1042', 'E03D.1047', or 'E03D.1051' and its progeny. For example, progeny produced by the methods described herein may be within 1, 2, 3, 4, or 5 breeding crosses of spinach hybrid 'E03D.1042', 'E03D.1047', or 'E03D.1051'.

As used herein, the term "plant" includes the whole plant or any parts or derivatives thereof, that have the same genetic makeup as the plant from which it is obtained, such as plant organs (e.g., harvested or non-harvested leaves), plant cells, plant protoplasts, plant cell and/or tissue cultures from which whole plants can be regenerated, plant calli, plant cell clumps, plant transplants, seedlings, plant cells that are intact in plants, plant clones or micropropagations, or parts of plants (e.g., harvested cells, tissues or organs), such as plant cuttings, vegetative propagations, embryos, pollen, ovules, anthers, pistils, fruits, flowers, leaves, cotyledons, hypocotyl, seeds, clonally propagated plants, roots, root tips, stems, root tips, parts of any of these and the like. Also any developmental stage is included, such as seedlings, cuttings prior or after rooting, mature plants or leaves.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

DEPOSIT INFORMATION

Spinach Hybrid 'E03D.1042'

A deposit of the spinach hybrid 'E03D.1042' is maintained by Enza Zaden USA, Inc., having an address at 7 Harris Place, Salinas, Calif. 93901, United States. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 2500 seeds of spinach hybrid 'E03D.1042' were deposited on DATE according to the Budapest Treaty in the National Collection of Industrial, Food and Marine Bacteria Ltd (NCIMB Ltd), Ferguson Building, Craibstone Estate, Bucksburn, Aberdeen, AB21 9YA, United Kingdom. The deposit has been assigned NCIMB Number X1. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

Spinach Hybrid 'E03D.1047'

A deposit of the spinach hybrid 'E03D.1047' is maintained by Enza Zaden USA, Inc., having an address at 7 Harris Place, Salinas, Calif. 93901, United States. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 2500 seeds of spinach hybrid 'E03D.1047' were deposited on DATE according to the Budapest Treaty in the National Collection of Industrial, Food and Marine Bacteria Ltd (NCIMB Ltd), Ferguson Building, Craibstone Estate, Bucksburn, Aberdeen, AB21 9YA, United Kingdom. The deposit has been assigned NCIMB Number X2. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

Spinach Hybrid 'E03D.1051'

A deposit of the spinach hybrid 'E03D.1051' is maintained by Enza Zaden USA, Inc., having an address at 7 Harris Place, Salinas, Calif. 93901, United States. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 2500 seeds of spinach hybrid 'E03D.1051' were deposited on Feb. 12, 2020 according to the Budapest Treaty in the National Collection of Industrial, Food and Marine Bacteria Ltd (NCIMB Ltd), Ferguson Building, Craibstone Estate, Bucksburn, Aberdeen, AB21 9YA, United Kingdom. The deposit has been assigned NCIMB Number 43578. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

The invention claimed is:

1. A spinach seed designated as 'E03D.1051', representative sample of seed having been deposited under NCIMB Accession Number 43578.

2. A spinach plant produced by growing the seed of claim 1.

3. A plant part from the plant of claim 2, wherein said part is selected from the group consisting of a leaf, a shoot, a stem, and a portion thereof.

4. The plant part of claim 3, wherein said part is a leaf.

5. A spinach plant having all the physiological and morphological characteristics of the spinach plant of claim 2.

6. A plant part from the plant of claim 5, wherein said part is selected from the group consisting of a leaf, a shoot, a stem, and a portion thereof.

7. The plant part of claim 6, wherein said part is a leaf.

8. A pollen grain or an ovule of the plant of claim 2.

9. A tissue culture of the plant of claim 2, wherein the tissue culture is produced from a plant part selected from the group consisting of a leaf, a cotyledon, a meristem, an anther, a root, a pistil, a flower, a stem, a callus, a hypocotyl, and a portion thereof.

10. A spinach plant regenerated from the tissue culture of claim 9, wherein the plant has all of the morphological and physiological characteristics of a spinach plant produced by growing seed designated as 'E03D.1051', representative sample of seed having been deposited under NCIMB Accession Number 43578.

11. A method of vegetatively propagating a spinach hybrid designated as 'E03D.1051', said method comprising:
(a) collecting tissue capable of being propagated from a plant of hybrid spinach variety 'E03D.1051', a sample of 'E03D.1051' spinach seed having been deposited under NCIMB Accession Number 43578; and
(b) producing a rooted plant from said tissue.

12. A method of making spinach seeds, said method comprising crossing the plant of claim 2 with another spinach plant and harvesting seed therefrom.

\* \* \* \* \*